United States Patent [19]

Bloom, deceased et al.

[11] 4,251,617

[45] Feb. 17, 1981

[54] NOVEL SILVER COMPLEXING AGENTS

[75] Inventors: Stanley M. Bloom, deceased, late of Maban, Mass., by Arlene N. Bloom, executrix; Krishna G. Sachdev, Cambridge, Mass.

[73] Assignee: Polaroid Corporation, Cambridge, Mass.

[21] Appl. No.: 80,440

[22] Filed: Oct. 1, 1979

[51] Int. Cl.³ .................. G03C 5/54; G03C 5/38; G03C 1/06

[52] U.S. Cl. ..................... 430/234; 430/251; 430/428; 430/455; 430/456; 430/459; 430/599; 430/603; 430/607; 430/611

[58] Field of Search ............ 430/234, 251, 428, 455, 430/456, 459, 599, 603, 607, 611

[56] References Cited

U.S. PATENT DOCUMENTS

| | | | |
|---|---|---|---|
| 2,875,048 | 2/1959 | Haist et al. | 430/456 |
| 3,021,215 | 2/1962 | Williams et al. | 430/603 |
| 3,062,646 | 11/1962 | Dann et al. | 96/66 R |
| 3,232,759 | 2/1966 | White et al. | 430/234 |
| 3,625,697 | 12/1971 | Sato et al. | 430/599 |
| 3,716,361 | 2/1973 | Thiers et al. | 430/234 |
| 3,930,867 | 1/1976 | Bigelow | 96/107 |
| 3,975,423 | 8/1976 | Borror et al. | 96/61 R |
| 4,017,314 | 4/1977 | Blake | 96/66 R |

OTHER PUBLICATIONS

Tetrahedron Letters, Pelissard and Louis, vol. 45, pp. 4589-4592, (1972).
Inorganic Nuclear Chem. Letters, Louis et al., vol. 13, pp. 31-35.

*Primary Examiner*—Mary F. Downey
*Attorney, Agent, or Firm*—Gaetano D. Maccarone

[57] ABSTRACT

There are described novel acyclic silver complexing agents which are useful as silver halide solvents in photographic products, processes and compositions. Also disclosed are photographic compositions, products and processes in which the complexing agents are utilized.

9 Claims, No Drawings

NOVEL SILVER COMPLEXING AGENTS

BACKGROUND OF THE INVENTION

This application relates generally to photography and more particularly to novel silver complexing compounds which are useful in photographic products, processes and compositions.

Photographic processing compositions capable of forming water-soluble complex silver salts are known to be useful in many types of silver halide photography. In conventional or "tray" development, it is customary to fix the developed silver halide emulsion by applying a solution of silver halide solvent, i.e., silver halide complexing agent which forms a water-soluble silver complex with the residual silver halide. The water-soluble silver complex thus formed and excess silver halide solvent are then removed from the developed and fixed emulsion by washing with water.

Silver halide solvents also have been employed in monobaths where a single processing composition containing a silver halide developing agent, in addition to the silver halide solvent, is utilized for both developing and fixing an exposed photosensitive silver halide layer. Silver halide solvents also have been employed in diffusion transfer photographic processes. Such processes are now well known in the art; see, for example, U.S. Pat. Nos. 2,543,181; 2,647,056; 2,983,606; etc. In processes of this type, an exposed silver halide emulsion is treated with a processing composition whereby the exposed silver halide emulsion is developed and an imagewise distribution of diffusible image-forming components is formed in the unexposed and undeveloped portions of the silver halide emulsion. This distribution of image-forming components is transferred by imbibition to an image-receiving stratum in superposed relationship with the silver halide emulsion to provide the desired transfer image. In diffusion transfer processes where a silver transfer image is formed, processing is effected in the presence of a silver halide solvent which forms a diffusible complex with the undeveloped silver halide. The soluble silver complex thus formed diffuses to the superposed image-receiving layer where the transferred silver ions are deposited as metallic silver to provide the silver transfer image. In preparing silver prints in this manner, the image-receiving element preferably includes a silver precipitating agent, for example, heavy metal sulfides and selenides as described in U.S. Pat. No. 2,698,237.

The present invention is concerned with novel silver halide solvents and their use in photographic products, processes and compositions.

SUMMARY OF THE INVENTION

It is therefore the object of the invention to provide novel silver complexing agents which are useful as silver halide solvents.

It is another object of the invention to provide novel acyclic silver complexing agents.

It is a further object to provide photographic products, processes and compositions employing such silver halide solvents.

BRIEF SUMMARY OF THE INVENTION

These and other objects and advantages of the invention are accomplished by providing novel silver complexing agents which are useful as silver halide solvents in photographic products, processes and compositions and which are represented by the general formula:

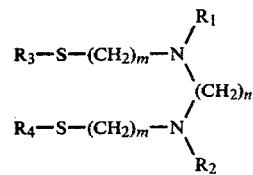

wherein m is 2 or 3; n is 2 or 3; $R_1$ and $R_2$ may be the same or different and may be H, alkyl, hydroxyalkyl or aminoalkyl having two to six carbon atoms; and $R_3$ and $R_4$ may be the same or different and may be alkyl, alkoxyalkyl, hydroxyalkyl or aminoalkyl having two to six carbon atoms.

DESCRIPTION OF THE PREFERRED EMBODIMENTS

Specific preferred silver complexing agents which are suitable for use according to the invention are represented by the following formulas:

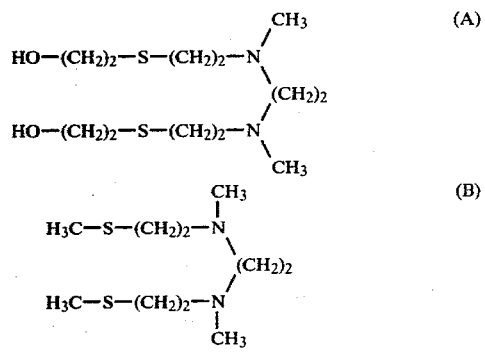

These preferred silver complexing agents are stable in an alkaline environment, have a melting point less than about 50° C. and the log of the stability constant ($\beta$) for a 1:1 complex of the complexing agent with silver is at least about 10.5. By "stable in an alkaline environment" is meant that the silver complexing agent retains at least 75% of its silver complexing ability after being in a 1 N sodium hydroxide solution for twenty-four hours at room temperature. These preferred complexing agents can be used in a diffusion transfer photographic method for making positive transparencies, without washing, which are substantially completely free of crystals. The method is described and claimed in applicants' copending application Ser. No. 080,349 filed on even date herewith.

Various of the novel compounds of the invention may be synthesized by reacting N,N'-dimethyl-N,N'-bis(2-mercaptoethyl)ethylenediamine (for its preparation see J. Amer. Chem. Soc., 98 6951 (1976) with the appropriate material, for example, ethylene oxide in aqueous solution to make compound A and methyl iodide-sodium hydride in tetrahydrofuran to form compound B.

The acyclic ligands wherein $R_1$ and $R_2$ are alkoxyalkyl can be prepared by initially reacting ethylenediamine with an alkoxyaldehyde to form a Schiff's base, reducing the Schiff's base to form the symmetrically substituted bis(alkoxyalkyl) ethylenediamine and reacting the latter with ethylene sulfide to form N,N'-dialkoxyalkyl-N,N'-bis(2-mercaptoethyl)ethylenediamine. Alkylation reactions of the latter may be carried out with alkylhalides, alkoxyalkylhalides, ethylene oxide and ethylene imine to obtain derivatives wherein $R_3$ and $R_4$ are alkyl, alkoxyalkyl, hydroxyalkyl and aminoalkyl. The analogous compounds wherein $R_1$ and $R_2$ are hydroxyalkyl can be prepared by starting with N,N'-bis(2-hydroxyalkyl)ethylenediamines, converting the hydroxyl groups to protect them such as by reacting with dihydropyran to form tetrahydroxypyranylether, followed by reaction with ethylene sulfide to form the desired N,N'-disubstituted-N,N'bis(2-mercaptoethyl)ethylenediamine. Alkylation of the latter with alkylhalides, alkoxyalkylhalides, ethylene oxide and ethylene imine may be employed to obtain derivatives wherein $R_3$ and $R_4$ are alkyl, alkoxyalkyl, hydroxyalkyl and aminoalkyl groups. After the ligands are isolated they are deblocked such as by acid hydrolysis. The primary amine aminoalkyl derivatives can be prepared by initially reacting ethylenediamine and a cyanoalkylaldehyde to form a Schiff's base, reducing the Schiff's base to form a symmetrically substituted cyanoalkyl ethylenediamine, and reacting the latter with ethylene sulfide to form the corresponding N,N'-bis(2-mercaptoethyl)ethylenediamines. The latter can be alkylated with various alkylating agents as described above followed by reduction of the cyano group to form the desired aminoalkyl substituted ligands. The tertiary amine aminoalkyl derivatives can be prepared by initially reacting ethylenediamine with a dialkylaminoalkylaldehyde to give a Schiff's base, reducing the Schiff's base to form a symmetrically substituted dialkylaminoalkyl ethylenediamine, reacting the latter with ethylene sulfide and reacting the product with alkylating agents to form the desired ligand. The desired ligands can be separated from the crude reaction products by first treating a methanol solution of the crude product with silver thiocyanate to form a 1:1 ligand—silver thiocyanate complex which preferentially crystallizes from solution while the impurities remain in the filtrate. Recrystallization of the complex followed by the precipitation of silver ions as silver sulfide with hydrogen sulfide and liberation of the free ligand by passing an aqueous solution of the resulting thiocyanic acid complex through an anion exchange column provides essentially pure samples of the ligands. Alternatively, purification can be effected by chromatography of the crude product mixture on silica gel, a more time-consuming procedure.

As mentioned previously, the compounds of the invention as represented by the general formula are useful as silver complexing agents in photography. The log of the stability constant ($\beta$) for a 1:1 complex of compound A is $10.91 \pm 0.01$ and that for compound B is $10.97 \pm 0.01$. The stability constants were determined by potentiometry, i.e., by titrating the ligand with a standardized solution of silver perchlorate in mildly alkaline, constant pH, constant ionic strength medium (0.05 M NaOH, 0.10 M NaClO$_4$). All solutions and titrants were prepared carbonate-free and with an ionic strength of 0.1 (NaClO$_4$). An argon atmosphere was used throughout. The indicating electrode was a silver specific ion type used in conjunction with a sleeve-type double-function Ag/Ag Cl reference electrode.

In formulating photographic processing compositions utilizing the above-described compounds, the compounds may be used singly or in admixture with each other or with other silver halide solvents. The total amount employed may vary widely depending upon the particular photographic system and should be used, for example, in a quantity sufficient for fixing a developed negative in conventional "tray" processing or in a quantity sufficient to give a satisfactory transfer print in diffusion transfer processes under the particular processing conditions employed.

Though the silver halide solvents of the present invention are broadly useful in a variety of photographic processes of the type in which water-soluble silver complexes are formed from the unreduced silver halide of a photoexposed and at least partially developed silver halide stratum, they find particular utility in diffusion transfer processes. A composition embodying the present invention specifically suitable for use in the production of transfer images comprises, in addition to the silver complexing agents of the above-described type, a suitable silver halide developing agent. Examples of developing agents that may be employed include hydroquinone and substituted hydroquinones, such as, tertiary butyl hydroquinone, 2,5-dimethyl hydroquinone, methoxyhydroquinone, ethoxyhydroquinone, chlorohydroquinone; pyrogallol and catechols, such as, catechol, 4-phenyl catechol and tertiary butyl catechol; aminophenols, such as, 2,4,6-triamino-orthocresol; 1,4-diaminobenzenes, such as, p-phenylenediamine, 1,2,4-triaminobenzene and 4-amino-2-methyl-N,N-diethylaniline; ascorbic acid and its derivatives, such as ascorbic acid, isoascorbic acid and 5,6-isopropylidene ascorbic acid, and other enediols, such as tetramethyl reductic acid; and hydroxylamines, such as, N,N-di-(2-ethoxyethyl)hydroxylamine and N,N-di-(2-methoxyethoxyethyl)hydroxylamine.

In diffusion transfer processes, the processing composition, if it is to be applied to the emulsion by being spread thereon in a thin layer, also usually includes a viscosity-imparting reagent. The processing composition may comprise, for example, one or more silver halide solvents of the present invention, one or more conventional developing agents such as those enumerated above, an alkali such as sodium hydroxide or potassium hydroxide and a viscosity-imparting reagent such as a high molecular weight polymer, e.g., sodium carboxymethyl cellulose or hydroxyethyl cellulose.

In one such transfer process, the processing solution is applied in a uniformly thin layer between the superposed surfaces of a photoexposed photosensitive element and an image-receiving element, for example, by advancing the elements between a pair of pressure-applying rollers. The elements are maintained in superposed relation for a predetermined period, preferably for a duration of 15 to 120 seconds, during which exposed silver halide is reduced to silver and unreduced silver halide forms a water-soluble, complex salt which diffuses through the layer of solution to the image-receiving element, there to be reduced to an argental image. At the end of this period, the silver halide element is separated from the image-receiving element. Materials useful in such a transfer process are well known in the art.

The photosensitive element may be any of those conventionally used in silver diffusion transfer processes and generally comprises a silver halide emulsion carried on a base, e.g., glass, paper or plastic film. The silver halide may be a silver chloride, iodide, bromide, iodobromide, chlorobromide, etc. The binder for the halide, though usually gelatin, may be a suitable polymer such as polyvinyl alcohol, polyvinyl pyrrolidone and their copolymers.

The image-receiving element preferably includes certain materials, the presence of which, during the transfer process has a desirable effect on the amount and character of silver precipitated on the image-receiving element. Materials of this type are known in the art.

Separating of the silver halide element from the image-receiving element may be controlled so that the layer of processing composition is removed from the image-receiving element or the layer of processing composition is caused to remain in contact with the image-receiving element, e.g., to provide it with a protective coating. Techniques which enable such results to be accomplished as desired are described in U.S. Pat. No. 2,647,054. In general, the processing reagents are selected so that traces remaining after the solidified processing layer has been separated from the silver image or which remain in said layer adhered as a protective coating on the silver image, as indicated above, are colorless or pale, so as not to appreciably affect the appearance of the image and to have little or no tendency to adversely react with the silver image.

The silver halide solvents of the present invention also may be employed in diffusion transfer processes adapted to provide positive silver transfer images which may be viewed as positive transparencies without being separated from the developed negative silver image including such processes adapted for use in forming additive color projection positive images. Diffusion transfer processes of this type are known in the art. See, for example, U.S. Pat. Nos. 3,536,488, 3,615,428 and 3,894,871. The subject compounds also find utility as silver halide solvents in diffusion transfer processes utilizing the properties of the imagewise distribution of silver ions in the soluble silver complex made available in the undeveloped and partially developed areas of a silver halide emulsion to liberate a reagent, e.g., a dye in an imagewise fashion, as described in U.S. Pat. No. 3,719,489.

As noted above, in diffusion transfer film units the negative component comprising at least one photosensitive layer and the positive component comprising an image-receiving layer may be in separate sheet-like elements which are brought together during processing and thereafter either retained together as the final print or separated following image formation.

Rather than the photosensitive layer and the image-receiving layer being in separate elements, they may be in the same element. In one such film unit, the image-receiving layer is coated on a support and the photosensitive layer is coated on the upper surface of the image-receiving layer. The liquid processing composition is applied between the combined negative-positive element and a second sheet-like element or spreading sheet which assists in spreading the liquid composition in a uniform layer adjacent the surface of the photosensitive layer.

Still other film units are those where the negative and positive components together may comprise a unitary structure wherein the image-receiving layer carrying the transfer image is not separated from the developed photosensitive layer(s) after processing, but both components are retained together as a permanent laminate. Such film units include those for providing positive silver transfer images which may be viewed as positive color transparencies, such as, those described in U.S. Pat. No. 3,894,871. Other integral film units also include those adapted for forming a transfer image, in color or in black and white, viewable by reflected rather than by transmitted light. In addition to the aforementioned photosensitive layer(s) and image-receiving layer, such film units include means for providing a reflecting layer between the image-receiving and photosensitive layer(s) in order to mask the developed photosensitive layer(s) and to provide a white background for viewing the transfer image. This reflecting layer may comprise a preformed layer of a reflecting agent included in the film unit or the reflecting agent may be provided subsequent to photoexposure, for example, by including the reflecting agent in the processing composition. In addition to these layers, the laminate usually includes dimensionally stable outer layers or supports, at least one of which is transparent so that the resulting transfer image may be viewed by reflection against the background provided by the light-reflecting layer. Integral negative-positive film units wherein the photosensitive and image-receiving layers are retained as a permanent laminate after processing are described, for example, in U.S. Pat. Nos. 3,415,644; 3,647,437; and 3,594,165.

It will be appreciated that in the formation of color transfer images, a dye image-providing material such as the compounds of U.S. Pat. No. 3,719,489 may be associated with the photosensitive silver halide layer or layers of the negative component.

The diffusion transfer film units described above are employed in conjunction with means, such as, a rupturable container containing the requisite processing composition and adapted upon application of pressure of applying its contents to develop the imagewise exposed film unit.

The invention will now be described further in detail with respect to specific preferred embodiments by way of examples, it being understood that these are illustrative only and the invention is not intended to be limited to the materials, conditions, process parameters, etc., recited therein. All parts and percentages are be weight unless otherwise indicated.

EXAMPLES

Preparation of N,N'-dimethyl-N,N'-bis(2-mercaptoethyl)ethylenediamine

A 250 ml three-neck flask, equipped with a magnetic stirrer, addition funnel, thermometer, and argon inlet was charged with a solution of 18.3 g (0.208 mol) of N,N'-methylethylenediamine in 70 ml of benzene. A solution of 25.1 g (0.417 mol) of ethylene sulfide in 10 ml of benzene was added with stirring over a two-hour period to the solution in the flask under argon while maintaining the temperature of the solution in the flask at 50°–55° C. The resulting clear solution was allowed to remain overnight at ambient temperature, washed with two 5 ml portions of water and dried over magnesium sulfate. The solvent was removed under reduced pressure and 39.9 g (97% yield) of a colorless oil were obtained.

The material is susceptible to air oxidation and therefore further purification was not carried out. The material can be stored up to a week under argon in a freezer without any significant deterioration. Since the compound has an extremely unpleasant odor and can cause severe skin allergy, careful handling is necessary.

EXAMPLE I

Preparation of Compound A

A 500 ml hydrogenation bottle placed in a 5° C. cooling bath was charged with 6.3 g (30 m mol) of freshly prepared N,N'-dimethyl-N,N'-bis(2-mercaptoethyl)ethylenediamine in 35 ml of carbonate-free water. To the resulting aqueous suspension there were added rapidly, with vigorous stirring, 3 ml (60 m mol) of ethylene oxide. The bottle was stoppered tightly and the contents allowed to stir for about 8 hours at 5° C. and then for another 8 hours at 25° C. The $^{13}$C NMR spectrum of the resulting aqueous solution showed six major lines expected for the desired ligand (compound A) accompanied by about 15–20% of unidentified impurities. Removal of the solvent under reduced pressure gave a colorless syrup which was dissolved in 75 ml of dichloromethane, washed with two 5 ml portions of water, dried over magnesium sulfate and concentrated to provide 6.5 g of a syrupy product. This product solidified upon being stored overnight in a refrigerator. Thin-layer chromatography on silica gel (in methanol) showed one major spot accompanied by traces of more polar impurities.

For further purification a 5.5 g sample of the crude material was stirred with 100 ml of ether until a fine, uniform suspension was formed. The suspension was kept at 0° C. for about 2 hours in an ice bath, the solid was filtered, washed with four 10 ml portions of ether and dried in vacuo to give 3.7 g of the ligand (compound A)—a colorless solid m.p. 43°–44° C. NMR spectra were consistent with the assigned structure. The mass spectrum showed a weak m/e at 296 for the parent ion with a strong P+1 at 297.

To assure the removal of any last traces of impurities, a small sample of the ligand was chromatographed on silica gel using ethyl acetate-methanol mixture or dichloromethane-methanol mixture as the elutant. After chromatographic separation the product was crystallized from ethyl acetate-petroleum ether mixture at −15° C. to furnish pure ligand as colorless needle-like crystals, m.p. 44°–45° C. $C_{12}H_{28}N_2S_2O_2$ requires 48.61% C, 9.52% H, 9.45% N, 21.63% S and 10.79% O. Elemental analysis gave 48.75% C, 9.60% H, 9.20% N and 21.53% S. NMR and mass spectral data were consistent with the desired ligand.

EXAMPLE II

Preparation of Compound B

To a 250 ml, three-neck flask equipped with a stirring bar, addition funnel, argon inlet and a rubber septum were added 3.98 g of 50% sodium hydride-oil dispersion. Most of the oil was removed by treating the dispersion with three 20-ml portions of petroleum ether under argon. 50 ml of dry tetrahydrofuran (99.9%) were then introduced into the dispersion from a syringe followed by a dropwise addition, with stirring, of 8.5 g (40 m mol) of N,N'-dimethyl-N,N'-bis(2-mercaptoethyl)ethylenediamine at a rate slow enough to keep frothing under control. The contents of the flask were allowed to stir for an additional 15 minutes and then treated with a solution of 10.96 g (80 m mol) methyl iodide in 7 ml tetrahydrofuran, added dropwise with vigorous stirring over a period of about 30 minutes. Throughout the addition the temperature was maintained below 30° C. by occasional cooling in an ice bath. The resulting reaction mixture was allowed to stir at ambient temperature for 14 hours. Excess sodium hydride was then destroyed with 5 ml of cold water and the solvent removed under reduced pressure.

The residue was taken up in 50 ml of ether, stirred for about 5 minutes and filtered to remove the suspended solids which were then washed with three 10 ml portions of ether. The combined ether filtrate and washings were washed with three 5 ml portions of water to remove any inorganic salts and dried over magnesium sulfate. Removal of solvent under reduced pressure gave 7.9 g of an essentially colorless thin liquid. Thin-layer chromatography on silica gel with methanol showed one major spot accompanied by some minor polar impurities.

To a solution of 7.5 g of the product in 50 ml of methanol were added 5.1 g of silver thiocyanate in small portions with vigorous stirring. Initially, the silver salt appeared to go into solution quite rapidly; but toward the end of the addition, the rate of dissolution slowed considerably. The mixture was allowed to stir for 20 minutes after addition of the silver thiocyanate, diluted with 100 ml of methanol and filtered through Celite 542 (a diatomaceous earth filter material available from Johns-Manville) to remove insoluble material. The filtrate was concentrated under reduced pressure to about 30 ml and stored overnight in a refrigerator. Crystals developed and were collected and recrystallized twice from methanol to provide 4.7 g of nearly colorless solid m.p. 106°–107° C. $C_{11}H_{24}N_3S_3$ Ag requires 32.83% C, 6.01% H, 10.44% N, 23.90% S and 26.81% Ag. Elemental analysis gave 32.88% C, 5.89% H, 10.42% N, 23.72% S and 26.83% Ag. A $^{13}$C NMR spectrum was consistent with the compound B—silver thiocyanate complex.

4.5 g of the complex were then dissolved in 50 ml of 60:40 (vol/vol) dichloromethane-ether mixture. The solution was cooled in an ice bath and treated with hydrogen sulfide gas to precipitate silver as silver sulfide. Following complete precipitation stirring was carried out for 15 minutes. The contents were filtered through Celite 542 and the filtrate was concentrated under reduced pressure to give a clear liquid. The liquid was treated with a stoichiometric amount of aqueous tetramethylammonium hydroxide and the product was extracted with dichloromethane. The extract was washed with water and dried over magnesium sulfate. The solvent was removed under reduced pressure, and there were obtained 2.45 g of the ligand (compound B) as a clear, thin liquid. NMR spectra were consistent with the desired ligand.

EXAMPLE III

A film unit was prepared as follows: the light-sensitive element comprised a transparent polyester film base carrying on one surface an additive color screen of approximately 1000 triplets per inch of red, blue and green filter screen elements in repetitive side by side relationship; an approximately 4 micron thick polyvinylidene chloride barrier layer; a nucleating layer comprising 0.23 mg/ft$^2$ of palladium nuclei (as metal), 0.29 mg/ft$^2$ of gelatin, 0.35 mg/ft$^2$ of tin (as metal) and 0.47 mg/ft$^2$ of total chloride (associated with Pd and Sn); an interlayer of 2.21 mgs/ft$^2$ of deacetylated chitin, 0.645 mg/ft$^2$ of copper acetate (dihydrate), 0.178 mg/ft$^2$ of sodium acetate and 0.194 mg/ft$^2$ of alkyl phenoxy polyoxy ethylene glycol; a hardened gelatino silver iodobromo emulsion coated at a coverage of about 90 mgs/ft$^2$ of silver, 120 mgs/ft$^2$ of gelatin, 53 mgs/ft$^2$ of Dow-620 carboxylated styrene butadiene latex and 4.83 mgs/ft² of dioctyl ester of sodium succinic acid (a surfactant); and an antihalo topcoat of 300 mgs/ft² of gelatin, 175 mgs/ft² of Dow-620 carboxylated styrene butadiene latex, 0.3 mg/ft² of dioctyl ester of sodium succinic acid, 5.2 mg/ft² of pyridinium-bis-1,5(1,3-diethyl-2-thiol-5-barbituric acid) pentamethine oxanol, 7.0 mgs/ft² of 4-(2-chloro-4-dimethylamino benzaldehyde)-1-(p-phenylcarboxylic acid)-3-methyl pyrazolone-5 and 4.9 mgs/ft² of benzimidazole-2-thiol gold $Au^{+1}$ complex (as gold).

The cover sheet comprised a 4 mil thick polyethylene terephthalate photographic film support having a thin coating on one surface to prepare the support for coating. Coated on the support in the following order were:

1. An acid providing layer formed by combining 60 parts by volume of a 30% solution of the half butyl ester of ethylene maleic anhydride in methyl ethyl ketone and 40 parts by volume of a solution of 5.7% Butvar B-72 (available from Monsanto), 63.3% ethyl acetate and 31% n-butanol and coating the mixture on the support at a dry coverage of about 2.45 gms/ft²; and 2. A gelatin layer formed by coating a water solution containing 10% deionized gelatin and 0.05% Emulphor ON-870 (available from Antara Chemical Co.) to provide a dry coverage of about 1 gm/ft².

Film units as described above were exposed through the additive color screen to a step wedge and processed by spreading a layer of processing composition less than about 3 mils thick between the light sensitive element and the cover sheet. The processing compositions were prepared by adding 0.08725 g of compound A and 0.05405 of compound B, respectively, to 10 ml of the following formulation:

| | |
|---|---|
| Water | 82.36 g |
| Sodium hydroxide | 7.265 g |
| Hydroxyethyl cellulose | 2.811 g |
| Sodium sulfite | 2.54 g |
| Tetramethyl reductic acid | 3.17 g |
| Dodecyl-N,N-dipyridinum dibromide | 1.78 g |
| 4-aminopyrazolo(3,4-d)-pyrimidine | 0.016 g |
| 5-bromo-6-methyl-4-azabenzimidazole | 0.016 g |
| Thiazolidine-2-thione | 0.035 g |

After an imbibition period of about one minute the maximum and minimum densities for the resultant images were measured on a transmission densitometer. The results were as follows:

| Compound | | Red | Green | Blue |
|---|---|---|---|---|
| A | $D_{max}$ | 1.97 | 1.97 | 2.07 |
| | $D_{min}$ | 0.54 | 0.62 | 0.76 |
| B | $D_{max}$ | 1.49 | 1.51 | 1.68 |
| | $D_{min}$ | 0.48 | 0.57 | 0.69 |

The resultant images did not have any apparent crystals when inspected visually ten days after processing. The images were stored under ambient conditions during the interim.

It will be apparent that the relative proportions of the subject silver halide solvents and of the other ingredients of the processing compositions may be varied to suit the requirements of a given photographic system. Also, it is within the scope of this invention to modify the formulations set forth above by the substitution of alkalies, antifoggants and so forth other than those specifically mentioned. Where desirable, it is also contemplated to include in the processing compositions, other components as commonly used in the photographic art.

Although the invention has been described with respect to various preferred embodiments thereof, it is not intended to be limited thereto but rather those skilled in the art will recognize that modifications and variations may be made therein which are within the spirit of the invention and the scope of the claim.

What is claimed is:

1. A diffusion transfer photographic process comprising the steps of:
   (a) reacting exposed silver halide in an image-wise exposed photosensitive silver halide emulsion layer carried on a support with a silver halide developing agent in aqueous alkaline solution;
   (b) reacting unreduced silver halide in said photosensitive emulsion with at least one silver complexing compound to form a complex silver salt that is soluble in said alkaline solution, said silver complexing compound being represented by the formula:

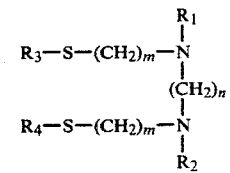

wherein m is 2 or 3; n is 2 or 3; $R_1$ and $R_2$ may be the same or different and may be H, alkyl, alkoxyalkyl, hydroxyalkyl or aminoalkyl having two to six carbon atoms; and $R_3$ and $R_4$ may be the same or different and may be alkyl, alkoxyalkyl, hydroxyalkyl or aminoalkyl having two to six carbon atoms, (c) transferring said silver complex salt to a superposed image-receiving layer; and
   (d) reducing said complex silver salt on said image-receiving layer to provide a silver image thereon.

2. The process as defined in claim 1 wherein said silver complexing compound is represented by the formula:

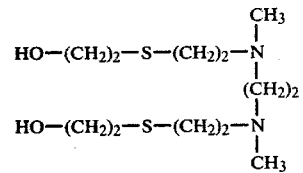

3. The process as defined in claim 1 wherein said silver complexing compound is represented by the formula:

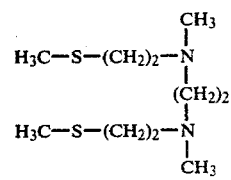

4. A photographic processing reagent comprising an aqueous alkaline solution containing at least one silver complexing compound which is represented by the formula:

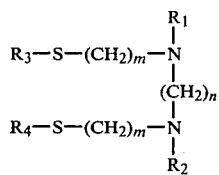

wherein m is 2 or 3; n is 2 or 3; $R_1$ and $R_2$ may be the same or different and may be H, alkyl, alkoxyalkyl, hydroxyalkyl or aminoalkyl having two to six carbon atoms; and $R_3$ and $R_4$ may be the same or different and may be alkyl, alkoxyalkyl, hydroxyalkyl or aminoalkyl having two to six carbon atoms.

5. A reagent as defined in claim 4 wherein said silver complexing compound is represented by the formula:

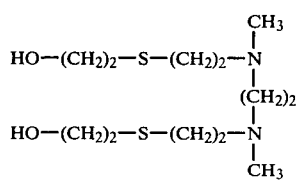

6. A reagent as defined in claim 4 wherein said silver complexing compound is represented by the formula:

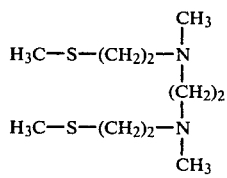

7. A photographic product comprising a support, a silver halide emulsion carried on said support and a silver complexing compound which is represented by the formula:

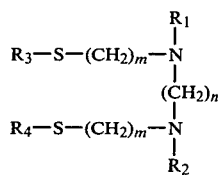

wherein m is 2 or 3; n is 2 or 3; $R_1$ and $R_2$ may be the same or different and may be H, alkyl, alkoxyalkyl, hydroxyalkyl or aminoalkyl having two to six carbon aoms, and $R_3$ and $R_4$ may be the same or different and may be alkyl, alkoxyalkyl, hydroxyalkyl or aminoalkyl having from two to six carbon atoms.

8. A product as defined in claim 7 wherein said compound is represented by the formula:

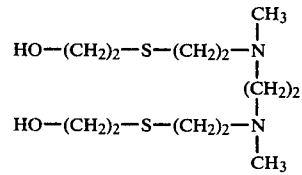

9. A product as defined in claim 7 wherein said compound is represented by the formula:

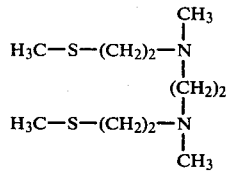

* * * * *